(12) United States Patent
Berkowitz

(10) Patent No.: US 10,369,336 B2
(45) Date of Patent: Aug. 6, 2019

(54) EXPANDABLE TISSUE DILATOR FOR DILATING TISSUE AROUND A SPINAL COLUMN

(71) Applicant: GLOBUS MEDICAL, INC., Audubon, PA (US)

(72) Inventor: Andrew Berkowitz, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 622 days.

(21) Appl. No.: 15/050,547

(22) Filed: Feb. 23, 2016

(65) Prior Publication Data

US 2017/0239451 A1    Aug. 24, 2017

(51) Int. Cl.
*A61M 29/02* (2006.01)
*A61B 17/34* (2006.01)

(52) U.S. Cl.
CPC ......... *A61M 29/02* (2013.01); *A61B 17/3421* (2013.01)

(58) Field of Classification Search
CPC .......................... A61M 29/02; A61B 17/3421
USPC .............. 606/108, 127, 192, 195, 198, 200; 623/1.11, 10
See application file for complete search history.

(56) References Cited

U.S. PATENT DOCUMENTS

| | | | |
|---|---|---|---|
| 6,436,119 B1 * | 8/2002 | Erb | A61B 17/3417 606/185 |
| 6,860,898 B2 * | 3/2005 | Stack | A61F 2/91 623/1.11 |
| 2010/0198149 A1 * | 8/2010 | Fox | A61B 17/3478 604/99.01 |
| 2015/0250992 A1 * | 9/2015 | Morriss | A61M 29/02 606/198 |

* cited by examiner

*Primary Examiner* — Vy Q Bui

(57) ABSTRACT

An expandable tissue dilator for dilating tissue around a spinal column includes a housing and a shaft at least partially positioned distally of the housing and adapted to pierce a tissue around the spinal column. An expandable member attached to the housing expands around a portion of the shaft to dilate the pierced tissue in a single-pass dilation resulting in a reduction of any traumatic impingement of nerves or muscle tissue and reduction in procedure time.

18 Claims, 4 Drawing Sheets

EXPANDABLE TISSUE DILATOR FOR DILATING TISSUE AROUND A SPINAL COLUMN

FIELD OF THE INVENTION

The present invention relates to a surgical apparatus, and more particularly to a dilator for dilating tissue around a surgical site.

BACKGROUND OF THE INVENTION

The development of minimally invasive percutaneous procedures has yielded a major improvement in reducing recovery time and post-operative pain because minimal dissection of tissue (such as the psoas muscle tissue, for example) is needed. Minimally invasive surgical techniques are desirable for spinal and neurosurgical applications because of the need for access to locations within the body, and the danger of damage to vital intervening tissues and nerves.

Surgical procedures within the body, especially near the spine, require a set of dilators and a retractor to clear the tissue surrounding the spine before the spine can be accessed. An access procedure for a surgical operation begins with the insertion of a guide wire followed by a series of successfully larger dilators installed in sequence to dilate the soft tissues such as the psoas muscle surrounding the spine. Then, following installation of the largest dilator deemed necessary, a retractor is advanced over the largest dilator for providing a working channel from the skin of the patient to working space adjacent the spine.

However, the set of conventional blunt dilators as described above has the potential to sever muscle fibers and irritate or otherwise disrupt the nerve roots which innervate the muscle tissue. This is especially true for dilating psoas muscle tissue to obtain access to the intervertebral disc space when performing a lumbar interbody fusion from a lateral approach.

Therefore, there is a need to provide an improved dilator and method for dilating the tissue with less muscle trauma and less damage to the nerve roots.

SUMMARY OF THE DISCLOSURE

An expandable tissue dilator for dilating tissue around a spinal column is provided. The dilator includes a housing and a shaft at least partially positioned distally of the housing and sufficiently stiff to pierce a tissue around the spinal column. An expandable member attached to the housing is expandable around a portion of the shaft to dilate the pierced tissue.

Advantageously, the expandable member of the dilator allows a single-pass dilation to occur instead of the conventional multi-pass dilation using multiple dilators. The single pass dilation reduces the likelihood of any traumatic impingement of nerves or muscle tissue and also reduces procedure time.

DETAILED DESCRIPTION OF THE INVENTION

Figure 1:
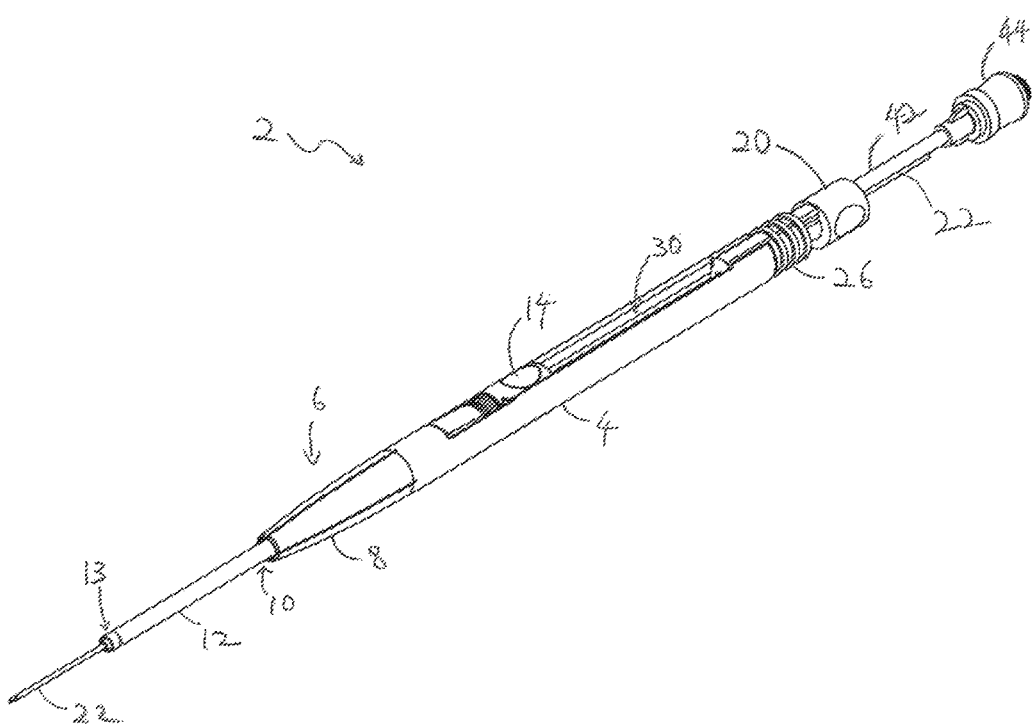
FIG. 1 is a perspective view of an expandable dilator according to an aspect of the present invention.

FIG. 1 is a perspective view of a dilator according to an embodiment of the present invention. The dilator 2 includes a housing 4 having a tapered tip section 6. The tip section 6 is preferably shaped as a partial cone and includes a plurality of circumferentially and uniformly spaced tapered flaps 8 whose distal ends define an end opening 10. In the embodiment shown, there are four uniformly spaced tapered flaps 8. However, any number of flaps are acceptable. The housing 4 including the tip section 6 can be made of plastic material such as ABS plastic.

An outer shaft such as a sheath 12 extends through the opening 10 of the housing 4 and its proximal end terminates at a sliding switch 14. The sheath 12 is sufficiently strong and rigid to pierce any muscle tissue such as psoas muscle that surrounds the vertebral column. The outer sheath 12 can be made of stainless steel, for example.

Figure 2A:
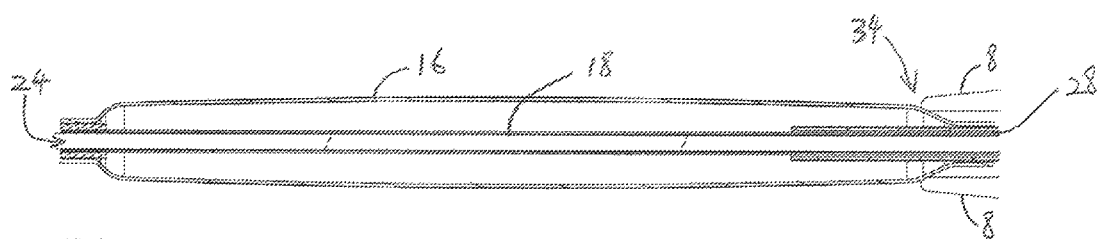
FIG. 2A is a cross-sectional view of a distal portion of the expandable dilator of FIG. 1.

The outer sheath 12 can be in an extended state to surround an expandable member 16 and a retracted state to expose the expandable member 16 for expansion against the muscle tissue. The outer sheath 12 is retractable by sliding the sliding switch 14 in the proximal direction. The retraction of the sheath 12 exposes the expandable member 16 such as a balloon (see FIG. 2A). Although the expandable member 16 is being referred to as a balloon 16, it is contemplated that expandable member 16 may be any structure capable of expanding. Referring to FIG. 2A, the balloon 16 is attached around an outer surface of an inner shaft such as an inner sheath 18 and is in fluid communication with an inflation lumen 28 that surrounds the inner sheath 18. The inner sheath 18 and the inflation lumen 28 extend through the housing 4 and terminate at a hub 20 which is attached to a proximal end of the housing 4. As shown, the balloon 16 is approximately 60 mm in length but other lengths are contemplated including lengths from 5 mm to 180 mm.

A tubing 42, in fluid communication with the inflation lumen 28, extends between the hub 20 and a luer connector 44. In operation, an inflation fluid source such as a fluid filled syringe (not shown) is connected to the connector 44 and provides the fluid for inflating the balloon 16.

The preferred inflation fluid depends on the type of imaging modality. When fluoroscopic imaging is used, an Iodine based contrast media or Gadolinium based contrast media can be used for improved visibility. Otherwise, saline solution or even water can be acceptable.

In the embodiment shown, the inner sheath 18 has a through-hole 24 for accommodating a guidewire 22 which is inserted through the through-hole 24 from the proximal end of the inner sheath. The distal end of the inserted guidewire 22 is inserted into a soft disc material within a vertebral column during the insertion and operation of the dilator 2. This facilitates docking of the dilator 2 with respect to the operative level to prevent inadvertent movement of the dilator 2.

The inner sheath 18 can be made of a single stainless steel tube, a steel coil reinforced TPU tube, or a steel reinforcing braid laminated between two TPU tube layers. Among others, the tube reinforcements serve two purposes. The first is to prevent occlusion of the inner lumen 18 when the balloon 16 is inflated to allow for positioning of the guide-wire 22 at any time throughout the procedure. The second is the reinforced or rigid steel tubing prevents axial growth of the balloon 16 when under pressure, so that expansion occurs generally radially.

An occlusion switch 26 slides along a distal portion of the hub 20 to seal an inflation lumen 28 (see FIG. 2A) once the balloon 16 has been inflated with the fluid as will be explained in more detail later herein.

As can be appreciated, the present invention provides several advantages over existing devices and methods for providing access to the intervertebral disc space. Using an expandable balloon to dilate the psoas muscle allows for a single-pass dilation to occur. This reduces the probability of any traumatic impingement of nerves or psoas muscle tissue during the initial insertion of the device. Also, by expanding the psoas muscle fibers from within (i.e., by expansion of the expandable member 16), the muscle fibers are more likely to be pushed aside, rather than punctured or severed. Additionally, due to the smooth transition point 34 at the distal end of the housing 4, the present invention is less susceptible to tissue creep whereas, in conventional systems, clearances were present between the sequential dilators. Furthermore, the present invention includes a single instrument that would take the place of several dilators. As a result, the present invention allows a reduction in procedural steps and consequently operative time.

Referring to FIG. 2A, the balloon 16 is a semi-compliant thermoplastic polyurethane (TPU) balloon which is in a partially expanded state. Prior to expansion, the balloon 16 is folded over the inner sheath 18 and enclosed within the outer sheath 12. As shown, the outer sheath 12 is a stainless steel sheath. The sheath 12 provides the necessary rigidity for dissection through soft tissue and muscle to the intervertebral disc.

The sheath 12 is coated with an electrically insulating layer, except at the distal end and proximal end. At the distal end, the insulating layer has been stripped from a small area 13 of between 1 and 3 mm in width such that it is electrically conductive. During insertion of the dilator 2, the conductive distal area 13 contacts the tissue as it is being dissected. The proximal end (electrically conductive portion) of the sheath 12 can be connected to a diagnostic device (not shown) to monitor any unusual electrical activity at the conductive area 13 in contact with the tissue which may indicate problems such as a pressed nerve.

Figure 2B:
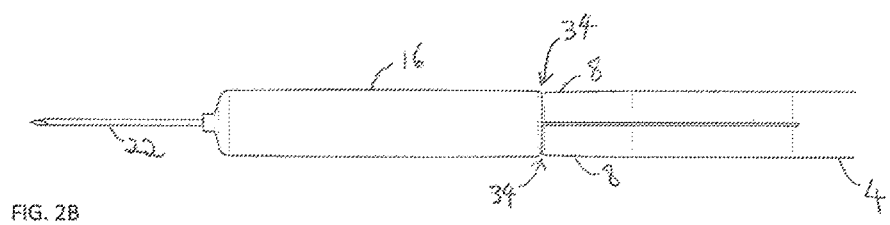
FIG. 2B is a side view of a distal portion of the dilator of FIG. 1 which has been expanded.

As shown in FIG. 2A, the balloon 16 has an inclined tapered portion at the proximal and distal ends. The distal ends of the flaps 8 of the tip section 6 are positioned to rest on the proximal portion of the balloon 16 and preferably on the inclined tapered proximal portion of the balloon. In its fully expanded state, the outer diameter of the balloon 16 closely matches that of the housing 4 (see FIG. 2B). As shown more clearly in FIG. 2B, as the balloon 16 expands, the flaps 8 resting on the balloon 16 also stretch and radially to provide a smooth transition point 34 and smooth surface along the length of the dilator 2 for a smooth insertion of a retractor over the dilator and minimal tissue creep. Preferably, the balloon 16 is either a semi-compliant or fully compliant balloon since the diameter of a fully expanded balloon is relatively definite.

As the expanding balloon applies substantial pressure against the inner sheath 18, the sheath is rated for (rated to withstand) at least 100 psi, and preferably at least 300 psi.

Figure 3:
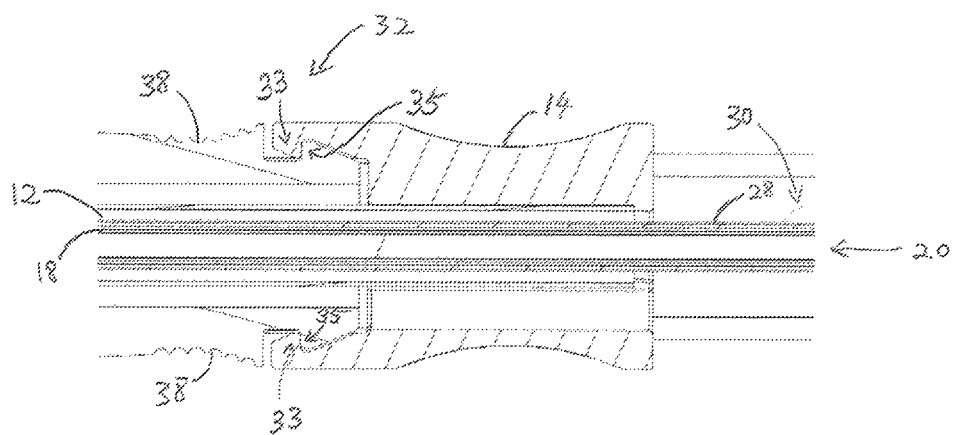
FIG. 3 is a cross-sectional view of a sliding switch of the dilator of FIG. 1.

FIG. 3 is a cross-sectional view of a sliding switch of the dilator of FIG. 1. The sliding switch 14 is attached to the outer surface of the outer sheath 12. The switch 14 is slidably received in a longitudinal recess 30 of the housing 4. When the switch 14 longitudinally slides along the recess 30 in a proximal direction, the outer sheath 12 is retracted to expose an uninflated balloon 16. Conversely, when the switch 14 slides in a distal direction, the outer sheath 12 slides over and covers the balloon 16 so that the balloon is protected when the dilator 2 is not being used. When the sliding switch 14 slides towards the distal end of the recess 30, a locking mechanism 32 locks the switch to the housing 4 to ensure that the outer sheath 12 covers and protects the uninflated balloon 16.

The locking mechanism 32 includes a pair of protrusions 33 extending radially inwardly from the switch 14 and a pair of hooks 35. The protrusion 33 extends radially inwardly while the hook 35 extends radially outwardly to mate with the protrusion to lock the sliding switch 14. The locking mechanism 32 further includes a pair of release buttons 38 attached to the housing 4 and coupled to the respective hooks 35. The release button 38 is biased away from the longitudinal axis of the housing 4 such that depression of the release button moves the hooks 35 radially inwardly and unlocks the sliding switch 14 from the housing 4.

Figure 4A:
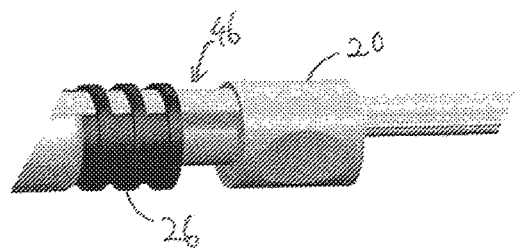
FIG. 4A is a perspective view of a sealing switch and hub of the dilator of FIG. 1.
Figure 4B:
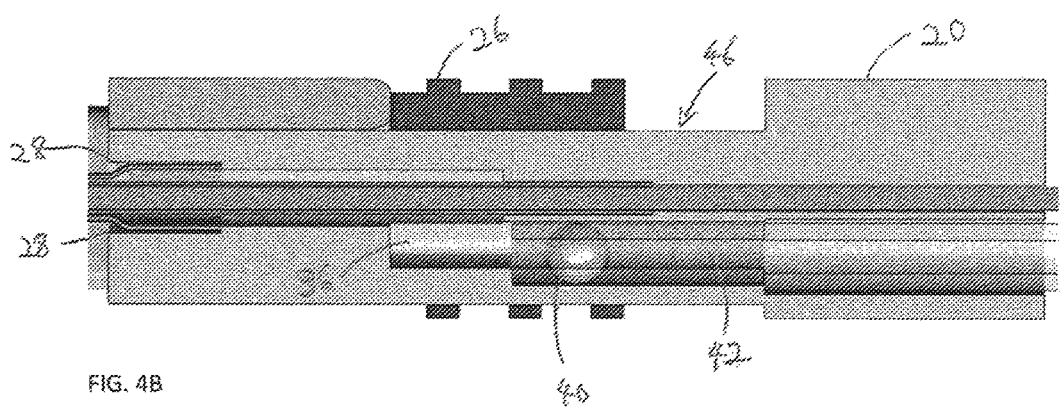
FIG. 4B is a cross-sectional view of the sealing switch and hub of the dilator of FIG. 1.
Figure 4C:
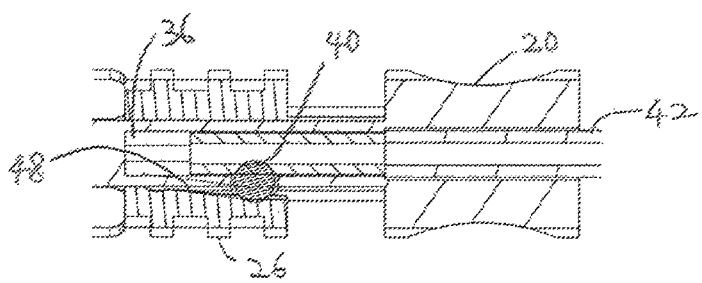
FIG. 4C is another cross-sectional view of the sealing switch and hub of the dilator of FIG. 1, which is rotated 90 degrees from that of FIG. 4B.

FIG. 4A is a perspective view of an occlusion switch 26 and hub 20 of the dilator of FIG. 1. A portion of a narrow distal portion 46 of the hub 20 is inserted into the proximal end of the housing 4 and is permanently affixed thereto with an adhesive. The occlusion switch 26 slides along the narrow distal portion 46 of the hub 20 to open and seal the inflation lumen 28 (see FIGS. 4B and 4C).

The hub contains a chamber 36 in fluid communication with the inflation lumen 28. A tubing 42 is in fluid communication with the chamber 36. An occluding ball 40 is positioned inside a lateral recess (not shown) and over the tubing 42. An inclined inner surface (ramp) 48 of the occlusion switch 26 is in contact with the occluding ball 40. When the occlusion switch 26 is moved proximally along the narrow portion 46, the inclined surface 48 presses the ball 40 radially inwardly which results in occluding the tubing 42. Since the tubing 42 is in communication with the inflation lumen 28 through the chamber 36, the proximal movement of the occlusion switch 20 seals the inflation lumen 28 from the inflation fluid source connected to the tubing 42. In effect, the inflation lumen, chamber 36 and tubing 42 are all a part of an inflation channel, and the occluding ball 40 can be positioned anywhere along the inflation channel.

With the outer sheath 12 retracted by the sliding switch 14, the balloon 16 is filled and pressurized with an inflation fluid which stretches the balloon and provides the necessary radial force to dilate the psoas muscle, while allowing for visualization under intra-operative fluoroscopic imaging. As the balloon 16 is expanded, the distal ends of the flaps 8 of the dilator 2 resting on the inclined surface of the balloon 16 will splay apart, maintaining a continuous outer surface free of any corners or edges. The distal ends of the flaps are also radiused to provide a smooth transition between the flaps and the expandable balloon. These features allow a retractor (not shown) to be smoothly introduced over the dilator 2.

When the balloon 16 is fully expanded, the occlusion switch 26 acts as a stopcock, maintaining pressure within the balloon and allowing the inflation device to be disconnected. In a spinal surgery, disconnecting the inflation device is necessary to allow for insertion of a retractor over the dilator 2.

A method of dilating the tissue will now be explained. First, a physician would make an incision of skin. Second, the dilator 2 is inserted through the incision and is slowly pushed through the muscle tissue while electrical activity from the electrically conductive tip 13 of the outer sheath 12 is monitored for any unusual activity. During the insertion step, the physician may need to reposition the dilator 2 depending on the electrical activity readings from the diagnostic device.

Third, a guidewire 22 is inserted through the through-hole 24 of the inner sheath 18 and its tip is inserted into the soft intervertebral disc space. Fourth, the outer sheath 12 is retracted to expose an uninflated balloon 16 by first depressing the release buttons 38 to release the lock, and then sliding the sliding switch 14 proximally while holding the housing 4 steady. Fifth, attach an inflation device such as a syringe to the connector 44 and inject an inflation fluid through the inflation lumen 28 to inflate the balloon 16. The expansion of the balloon 16 dilates the muscle tissue in contact with the dilator 2. Sixth, once the balloon 16 is inflated to a desired level or pressure, the inflation lumen 28 is occluded by using the occlusion switch 26. Seventh, a retractor is slid over the dilator 2 and expanded balloon 16. Eighth, the inserted retractor is then used to further dilate the muscle tissue to create a working channel into the surgical site.

Figure 5A:
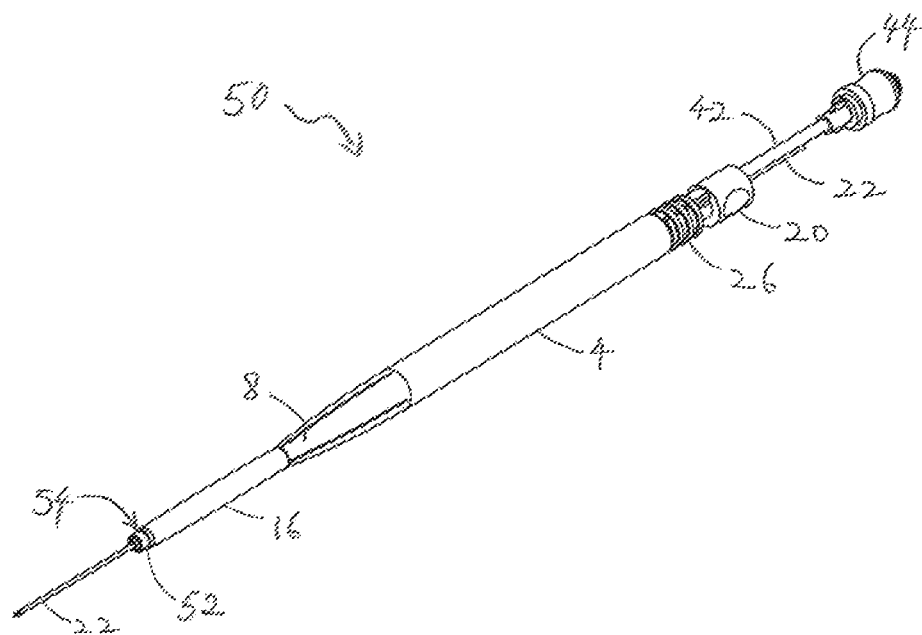
FIG. 5A is a perspective view of an expandable dilator according another aspect of the present invention.
Figure 5B:
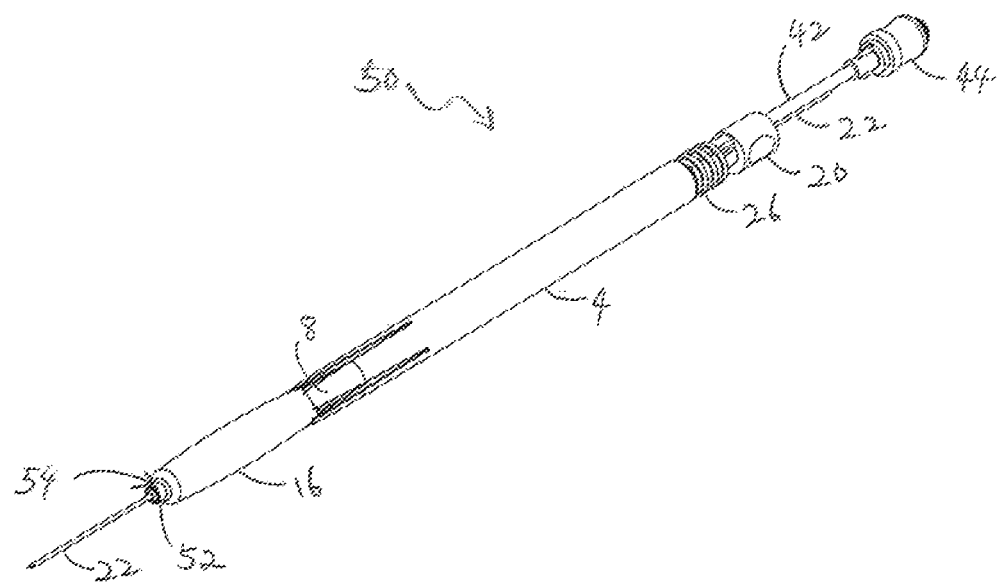
FIG. 5B is a perspective view of the dilator of FIG. 5A which has been expanded.

FIGS. 5A and 5B illustrate an expandable dilator according another aspect of the present invention. Unlike the dilator of FIG. 1, the dilator 50 does not have an outer sheath 12. An inner sheath/tube 52 to which the balloon 16 is attached is a slightly larger diameter and thicker sheath than the inner sheath 12 of FIG. 1. The inner sheath 52 is made of stainless steel, for example. The additional rigidity provided by the larger and thicker inner sheath 52 eliminates the need for an outer sheath 12. This simplified design does not require a sliding switch and therefore reduces the number of procedural steps. In the absence of an outer sheath 12, the inner tube 52 is coated in an insulating layer throughout its length, except the distal end which has a small conductive outer surface 54 and proximal end which also has a conductive area for connection to a diagnostic device for monitoring electrical activity near the distal tip of the inner sheath 52.

It is to be understood that the disclosure describes a few embodiments and that many variations of the invention can easily be devised by those skilled in the art after reading this disclosure and that the scope of the present invention is to be determined by the following claims.

What is claimed is:

1. An expandable tissue dilator for dilating tissue around a spinal column, comprising:
   a housing;
   a shaft adapted to be at least partially disposed distally of the housing and sufficiently stiff to pierce a tissue disposed around the spinal column;
   an expandable member attached to the housing and adapted to be expandable around a portion of the shaft which has pierced the tissue, the expandable member further comprising an inflation channel and an occlusion switch disposed in a proximal section of the housing and operable to occlude the inflation channel; and
   an occluding ball disposed over an inflation channel, wherein the occlusion switch has an inclined inner surface relative to a longitudinal axis of the inflation channel and is adapted to slide over the occluding ball such that the inner surface presses on the occluding ball to occlude the inflation channel.

2. The expandable tissue dilator of claim 1, wherein the expandable member includes a balloon attached to an outer surface of the shaft.

3. The expandable tissue dilator of claim 2, wherein the tapered tip section includes a plurality of circumferentially spaced tapered flaps that define an end opening through which the shaft extends, the distal ends of the flaps being positioned over the expandable member and sufficiently flexible to radially outwardly move as the expandable member expands.

4. The expandable tissue dilator of claim 3, wherein the distal ends of the flaps are radiused to provide a smooth transition between the flaps and the expandable member.

5. The expandable tissue dilator of claim 1, wherein the housing includes a tapered tip section having a distal end positioned over the expandable member.

6. The expandable tissue dilator of claim 1, wherein the housing has a longitudinal recess, further comprising:
   an inner sheath surrounded by the shaft, wherein the expandable member is attached over the inner sheath and underneath the shaft;
   a sliding switch attached to the shaft and operable to slide along the longitudinal recess to retract the shaft to expose the expandable member.

7. The expandable tissue dilator of claim 6, further comprising a locking mechanism that locks the sliding switch to the housing such that the shaft covers the expandable member.

8. The expandable tissue dilator of claim 7, wherein locking mechanism includes:
   a protrusion extending from the sliding switch;
   a hook adapted to mate with the protrusion to lock the sliding switch; and
   a release button attached to the housing and coupled to the hook such that depression of the release button unlocks the sliding switch from the housing.

9. The expandable tissue dilator of claim 1, wherein the expandable member is a balloon and the inflation channel is in fluid communication with the balloon.

10. An expandable tissue dilator for performing spinal surgery, comprising:
    an elongate housing;
    an inner sheath at least partially disposed in the housing and having a distal portion that extends distally of the housing, the inner sheath being sufficiently stiff to pierce a muscle tissue around a spinal column;
    an expandable member attached around an outer surface of the inner sheath and being expandable to radially push the pierced muscle tissue, the expandable member further comprising an inflation lumen and an occlusion switch disposed in a proximal section of the housing and operable to occlude the inflation lumen; and
    an occluding ball disposed over an inflation lumen, wherein the occlusion switch has an inclined inner surface relative to a longitudinal axis of the inflation lumen and is adapted to slide over the occluding ball such that the inner surface presses on the occluding ball to occlude the inflation lumen; and a retractable outer sheath surrounding the inner sheath and configured to be in an extended state to surround the expandable member and a retracted state to expose the expandable member for expansion against the pierced muscle tissue.

11. The expandable tissue dilator of claim 10, wherein the expandable member includes a balloon attached to an outer surface of the inner sheath.

12. The expandable tissue dilator of claim 10, wherein the housing includes a tapered tip section having a distal end positioned over the expandable member.

13. The expandable tissue dilator of claim 12, wherein the housing tip section includes a plurality of circumferentially spaced tapered flaps that define an end opening through which the inner sheath extends, the distal ends of the flaps being positioned over the expandable member and sufficiently flexible to radially outwardly move as the expandable member expands.

14. The expandable tissue dilator of claim 13, wherein the distal ends of the flaps are radiused to provide a smooth transition between the flaps and the expandable balloon.

15. The expandable tissue dilator of claim 10, wherein the housing has a longitudinal recess, further comprising a sliding switch attached to the outer sheath and operable to slide along the longitudinal recess to retract the outer sheath to expose the expandable member.

16. The expandable tissue dilator of claim 15, further comprising a locking mechanism that locks the sliding switch to the housing such that the outer sheath is in the extended state.

17. The expandable tissue dilator of claim 16, wherein locking mechanism includes:
 a protrusion extending from the switch;
 a hook adapted to mate with the protrusion to lock the sliding switch; and
 a release button attached to the housing and coupled to the hook such that depression of the release button unlocks the sliding switch from the housing.

18. The expandable tissue dilator of claim 10, wherein the expandable member is a balloon and the inflation lumen in fluid communication with the balloon.

\* \* \* \* \*